(12) United States Patent
Reilly et al.

(10) Patent No.: US 6,770,454 B2
(45) Date of Patent: Aug. 3, 2004

(54) METHOD FOR DETECTING MICROORGANISMS

(75) Inventors: Sean M. Reilly, East Stroudsburg, PA (US); Paul T. LaRocca, Sparta, NJ (US); Mary Anne Kunz LaRocca, Sparta, NJ (US)

(73) Assignee: Home Health Science Inc., Sparta, NJ (US)

( * ) Notice: Subject to any disclaimer, the term of this patent is extended or adjusted under 35 U.S.C. 154(b) by 367 days.

(21) Appl. No.: 09/826,045

(22) Filed: Apr. 4, 2001

(65) Prior Publication Data

US 2001/0041352 A1 Nov. 15, 2001

Related U.S. Application Data

(60) Provisional application No. 60/194,666, filed on Apr. 4, 2000.

(51) Int. Cl.[7] .................................................. C12Q 1/04
(52) U.S. Cl. .......................................... 435/34; 435/30
(58) Field of Search ............................ 435/34, 30, 40, 435/287.4, 288.7, 171, 911

(56) References Cited

U.S. PATENT DOCUMENTS

| | | | |
|---|---|---|---|
| 3,956,070 A | 5/1976 | Kenyon | 195/103.5 |
| 3,968,012 A | 7/1976 | Jones | 195/142 |
| 3,980,524 A | 9/1976 | Reuter | 195/139 |
| 4,539,256 A | 9/1985 | Shipman | 428/315.5 |
| 4,565,783 A | 1/1986 | Hansen et al. | 435/299 |
| 4,587,213 A | 5/1986 | Malecki | 435/39 |
| 5,089,413 A | 2/1992 | Nelson et al. | 435/254.1 |
| 5,137,812 A | 8/1992 | Matner | 435/38 |
| 5,232,838 A | 8/1993 | Nelson et al. | 435/30 |
| 5,525,397 A | 6/1996 | Shizuno et al. | 428/138 |
| 5,635,367 A | 6/1997 | Lund | 435/34 |
| 5,681,712 A | 10/1997 | Nelson | 435/30 |
| 6,040,153 A | 3/2000 | Lemonnier | 435/30 |
| 6,054,324 A * | 4/2000 | Sullivan et al. | 436/174 |

FOREIGN PATENT DOCUMENTS

WO        98/31785        7/1998

\* cited by examiner

*Primary Examiner*—Ralph Gitomer
(74) *Attorney, Agent, or Firm*—Synnestvedt & Lechner LLP

(57) ABSTRACT

The specification relates to a method for the detection and collection of samples of microorganisms, such as mold spores, from the air and from surfaces utilizing a collection device that employs a substantially dry growth medium which is hydrated by a premeasured volume of liquid after microorganism collection on the dry growth medium has occurred. The specification also relates to a microorganism collection and detection kit comprising a microorganism collection device having a substrate and a layer of dry growth medium applied thereon, and a container of a premeasured volume of hydrating liquid.

10 Claims, 6 Drawing Sheets

*FIG.8*
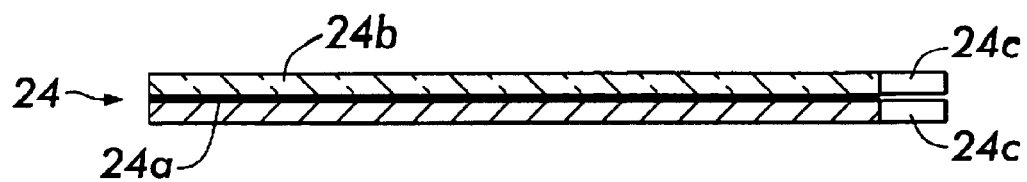
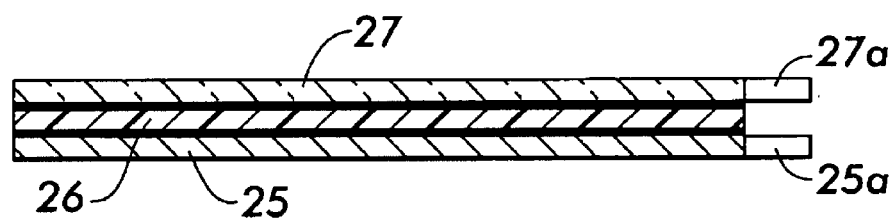
*FIG.9*
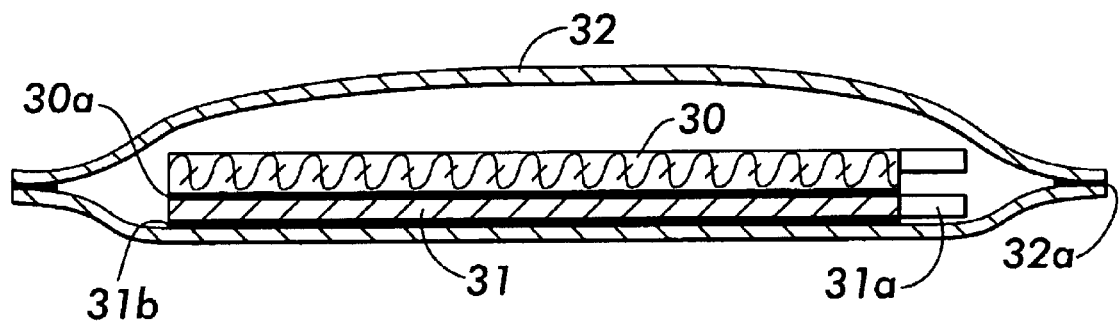
*FIG.10*

METHOD FOR DETECTING MICROORGANISMS

CROSS-REFERENCE TO RELATED APPLICATIONS

This application is based on a Provisional Application, Ser. No. 60/194,666, filed on Apr. 4, 2000.

FIELD OF THE INVENTION

This invention relates to a method and a kit for the detection and collection of microorganisms from the air and from surfaces utilizing a collection device that employs a dry collection methodology and a dry growth medium, and a container of a premeasured volume of liquid for hydrating the dry growth medium after microorganism collection on the dry growth medium has occurred.

BACKGROUND OF THE INVENTION

Many molds are considered to be harmful microorganisms. Mold spores are minute propagating units that facilitate the growth and spread of mold colonies. Inhalation of mold spores and other microorganisms into the lungs of humans has been found to be a significant factor in causing a number of different pneumoconioses and other health problems such as allergies, headaches, and fatigue. Most molds require oxygen and water to live and the aerobic molds of our environment are known to multiply and migrate by producing and releasing millions of mold spores into the air.

Methods for estimating the relative environmental mold spore bioburden count exist, but these methods involve the collection of environmental air mold spores on wet media such as Sabouraud's Dextrose Agar (an aqueous suspension of gelatin and nutrients that solidifies to a semi-solid, water-based gel below 45° C.). Exposing sterile Sabouraud Dextrose Agar in an open container such as a petri dish to air containing mold spores can result in mold spores settling on the agar on which they can then germinate and grow. After a number of days, the colonial growth resulting from the germination of a single spore may be so large that the colony may be visually discernable without the use of magnification equipment.

An example of the device described above is disclosed in U.S. Pat. No. 3,968,012 which provides a device for detecting bacteria and other microorganisms carried in the air inside of hospital respiratory machines, such as ventilators and anesthesia gas machines. The device comprises a culture medium dish, a cylindrical casing, and a sanitary cover where the dish and cover are substantially similar to a petri dish. In operation, the device is attached to the vent of a respiratory machine, and the cylindrical casing controls the flow of the air to the medium dish so that microbial particles are collected from the air.

Many other devices in the prior art combine machinery with wet culture media to sample air for testing. For example, U.S. Pat. No. 3,956,070 discloses a device comprising a casing to direct a flow of air over a cartridge containing a culture medium. The cartridge is comprised of a two-sided strip that is wound around two reels with a culture medium spread over each side of the strip. In operation, air is vented through the casing and over both sides of the culture medium strip. U.S. Pat. No. 3,980,524 discloses a device resembling the shape of a common flashlight which comprises a casing that houses batteries, a motor with a drive-shaft and flanges, and a culture medium cup. In this device, the motor is employed with the drive-shaft and flanges to direct a volume of air over the medium cup.

Dry growth media has been used to detect microorganisms in liquid samples. U.S. Pat. No. 4,565,783 discloses a device for growing microorganisms, comprising a self-supporting water-proof substrate, a layer of adhesive coated thereon, and a coating of dry, cold-water-soluble growth medium powder adhered uniformly to the surface of the adhesive. In accordance with the teachings of U.S. Pat. No. 4,565,783, when an aqueous test sample is placed on the substrate in contact with the dry growth medium powder, the growth medium is hydrated to a gel and germination of microorganisms present in the test sample may result.

Since environmental mold spores are and have been associated with adverse health effects in humans, it is desirable to monitor the environmental mold spore bioburden count in dwellings, office buildings, schools and other indoor areas inhabited by people. Various health organizations routinely monitor environmental air in specific locations for mold spores using passive and active agar impaction methods, however, these organizations generally do not test individual homes, businesses, churches, etc. There are health professionals who, for a fee, monitor the air for environmental mold spores in an individuals most frequently inhabited environments, but fees are high and anonymity may not be maintained during and/or after the testing.

Establishing the environmental mold spore count by moist agar impaction methods utilizing Sabouraud Dextrose Agar or other known nutrient formulations, for example trypticase soy agar as disclosed in U.S. Pat. No. 3,968,012, has many associated problems. The first problem is that sealed agar plates utilized in moist agar impaction methods have a relatively short shelf life, on the order of a few weeks at most. Further, moist agar can lose its moisture rapidly over time and, as a result, its ability to support microorganism germination and growth decreases rapidly to a point where germination may not occur at all.

In addition, the use of moist agar to collect environmental mold spores may create what can be described as a time lag problem. An environmental mold spore impacting an unsealed hydrated microbiological growth medium during the first moments of exposure, i.e., the first minute in a 60-minute exposure, may enjoy distinct survival advantages as compared to an environmental mold spore impacting a desiccated microbiological growth medium during the last moments of the exposure as a direct result of changes in moisture conditions of the growth medium over the exposure interval. The latter arriving spores may geminate only very slowly producing a micro-colony that may be too small to be visually enumerated, or may not even germinate at all. An undercount of the actual population of spores can result producing an inaccurate assessment of the true population of environmental mold spores in the location under analysis.

The known methods of the prior art typically employed in air quality sampling are the use of passive agars in petri dishes or agars which are inserted into active volumetric pump samplers. The use of agars in air quality sampling has multiple impediments for the individual consumer/user, including increased costs for preparation and storage and shipping, a very short shelf life and, if active volumetric pump samplers are used, an extremely high purchase cost or rental cost.

SUMMARY OF THE INVENTION

A useful method of environmental air and surface sampling which comprises the dry collection and subsequent hydration, growth and enumeration of microorganisms has been discovered. The use of such procedures has been found to overcome the problems of time-lag growth disparities and evaporation of the activating liquid during collection identified above. In addition, dry collection devices exhibit a relatively long shelf-life and provide the added advantage of being easier to handle, especially at the extremes of normal ambient temperatures. The dry collection method of the present invention is accomplished by means of an easy to use, low cost home test kit to quantify the environmental mold spore and microorganism count and represents an important step in the reduction of environmental microorganism levels. Such a kit is also useful to educators teaching concepts of microbiology and mathematics. The method and kit is also a tool for use in monitoring work environments including commercial/industrial facilities.

One aspect of the present invention is a method of detecting microorganisms comprising the steps of exposing a dry collection device containing a dry growth medium to environmental microorganisms, adding a premeasured volume of liquid to the dry growth medium, and allowing collected microorganisms to grow into colonies. In certain embodiments, the exposure step may be accomplished by placing the collection device on a surface for a predetermined interval of time so that microorganisms in the air can settle out onto the collection device. Alternatively, the exposure step may also be accomplished by the direct application of a dry adhesive collection device to a surface so that microorganisms located on the surface can be captured and transferred directly to the dry growth medium prior to hydration. While the step of adding a premeasured volume of liquid to the dry growth medium can be accomplished in a variety of ways all of which are considered to be within the scope of the invention, it is preferred that the liquid is applied so that only a predetermined area of the dry growth medium is hydrated. In such a fashion, the subsequent counting of microorganism colonies can be accomplished with respect to a standardized counting area and populations can be expressed in terms of colonies per unit area. One preferred technique for hydrating the dry growth medium involves the use of a hand press in which the press is placed on the cover over the liquid after its application to the dry growth medium and pressure is applied thereto sufficient to spread the liquid out over a predetermined area of the dry growth medium.

The growth step of the method of the present invention is accomplished by allowing a sufficient interval of time to elapse to permit the growth of microorganism colonies and, depending on the growth characteristics of particular microorganisms which are being detected, can involve the placement of the hydrated collection device in an ambient environment or in a non-ambient environment such as, for example, an incubator. Certain embodiments of the method of the invention further comprise the step of counting the colonies of microorganisms that have grown on the growth medium device after its exposure to air and after hydration of the dry growth medium. The results from the count can then be analyzed in accordance with a variety of parameters known in the art.

Another aspect of the present invention is a kit comprising a microorganism collection device having a substrate and a layer of dry growth medium applied thereon, and a container of a premeasured volume of liquid for hydrating the dry growth medium once collection of microorganisms has occurred. In certain embodiments, the substrate of the device is waterproof and self-supporting, while in other embodiments the substrate is in the form of a tape comprising a non-porous layer and a micro-porous layer adhesively attached thereto. The dry growth medium applied thereon is preferably soluble in cold or ambient water and in the form of a powder. The powder may comprise a gelling agent in sufficient amount to provide a gel having a Brookfield viscosity of at least 1500 cps when hydrated with a premeasured amount of water. The dry growth medium may have sufficient inherent adhesive characteristics such that it may be adhered directly to the substrate. Alternatively, the bond between the dry growth medium and the substrate may be facilitated by means of an adhesive pre-applied to the substrate or by mixing the dry growth medium with an adhesive prior to application to the substrate. In another embodiment, the collection device further comprises an air-permeable membrane. The membrane may improve the growth of certain aerobic microorganisms if the growth medium is covered after exposure and hydration.

In certain embodiments, the collection device may further comprise a cover sheet releasably adhered to at least a portion of the substrate. The cover sheet is opened in the first step of the method to expose the dry growth medium to the environment, and then the cover sheet is closed after the liquid is added to the medium and before the liquid is spread over the medium. The cover sheet serves several functions including the protection of the dry growth medium from unintended premature exposures, the retention of microorganisms once the collection step is completed, the retention of moisture once the hydrating liquid has been applied to the dry growth medium, and the preservation of the culture upon completion of microorganism colony growth.

In certain embodiments, the kit further comprises a hand press for applying the premeasured volume of liquid to a predetermined area of the dry growth medium. While the press may assume a variety of configurations that will accomplish the distribution of the liquid over the dry growth medium, the press preferably will comprise a pressing surface and a raised ring on the pressing surface defining a predetermined area such that the application of the press to the liquid on the growth medium results in the spreading out of the liquid to the full extent of the predetermined area. The resulting area in which the growth medium is hydrated allows for standardized counting so that microorganism populations can be expressed in terms of colonies per unit area. The kit of the invention can assume various configurations based on the needs and desires of the user as the kits may be tailored specifically for home, commercial/industrial, or office use and have applicability as well as teaching aids in schools and particularly for science instruction, all of which are considered to be within the scope of the invention.

The kit of the device is particularly intended for use by consumers without need for assistance or employment of a microbiologist, laboratory technician or other skilled personnel The implementation of the quantifiable collection of environmental microorganisms from air and surfaces is made much more cost effective by employment of the collection methodology of the invention.

BRIEF DESCRIPTION OF THE DRAWINGS

The invention may be further illustrated by reference to the accompanying drawings wherein:

FIG. 8 is a cross sectional view of a single layer, non-porous plastic tape.

FIG. 9 is a cross sectional view of the tape shown in FIG. 8 with an additional micro-porous layer.

FIG. 10 is a cross sectional view of a filter pad placed within an enclosure.

DESCRIPTION OF THE PREFERRED EMBODIMENTS

Figure 1:
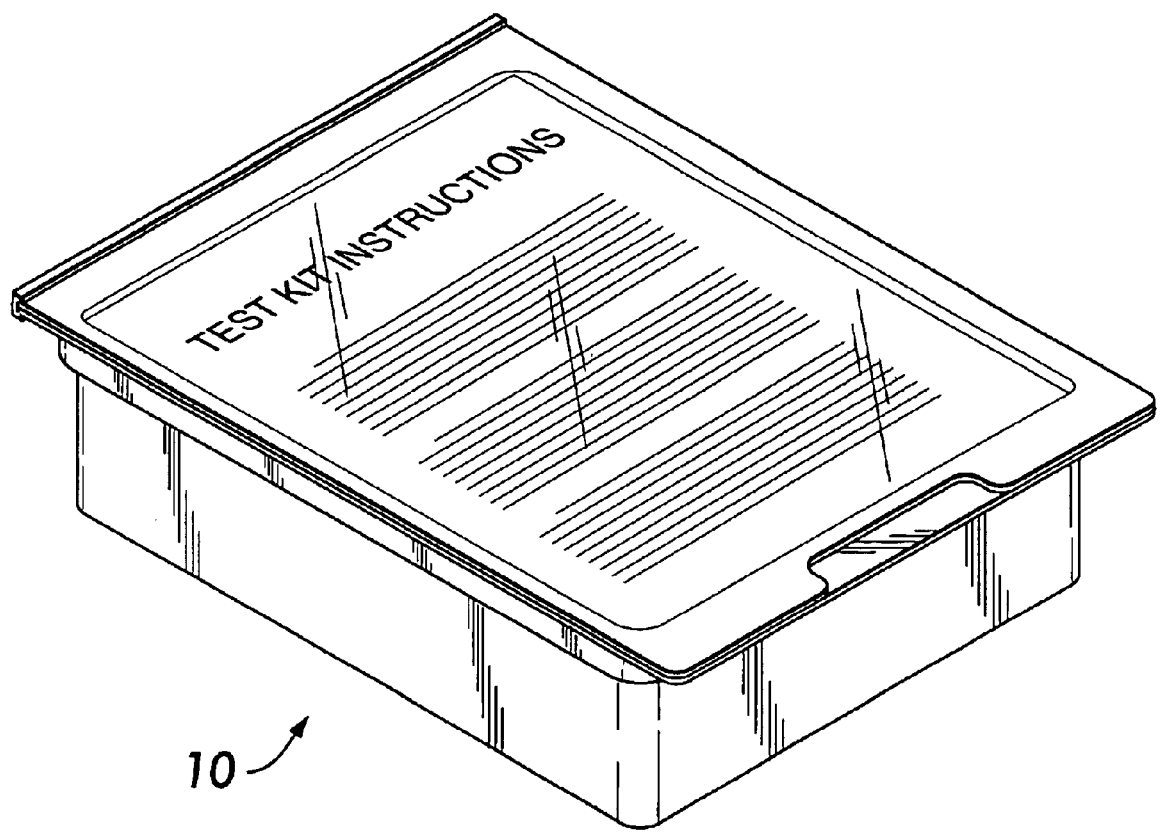
FIG. 1 is a top perspective view of a preferred embodiment of a collection kit according to the present invention.
Figure 2:
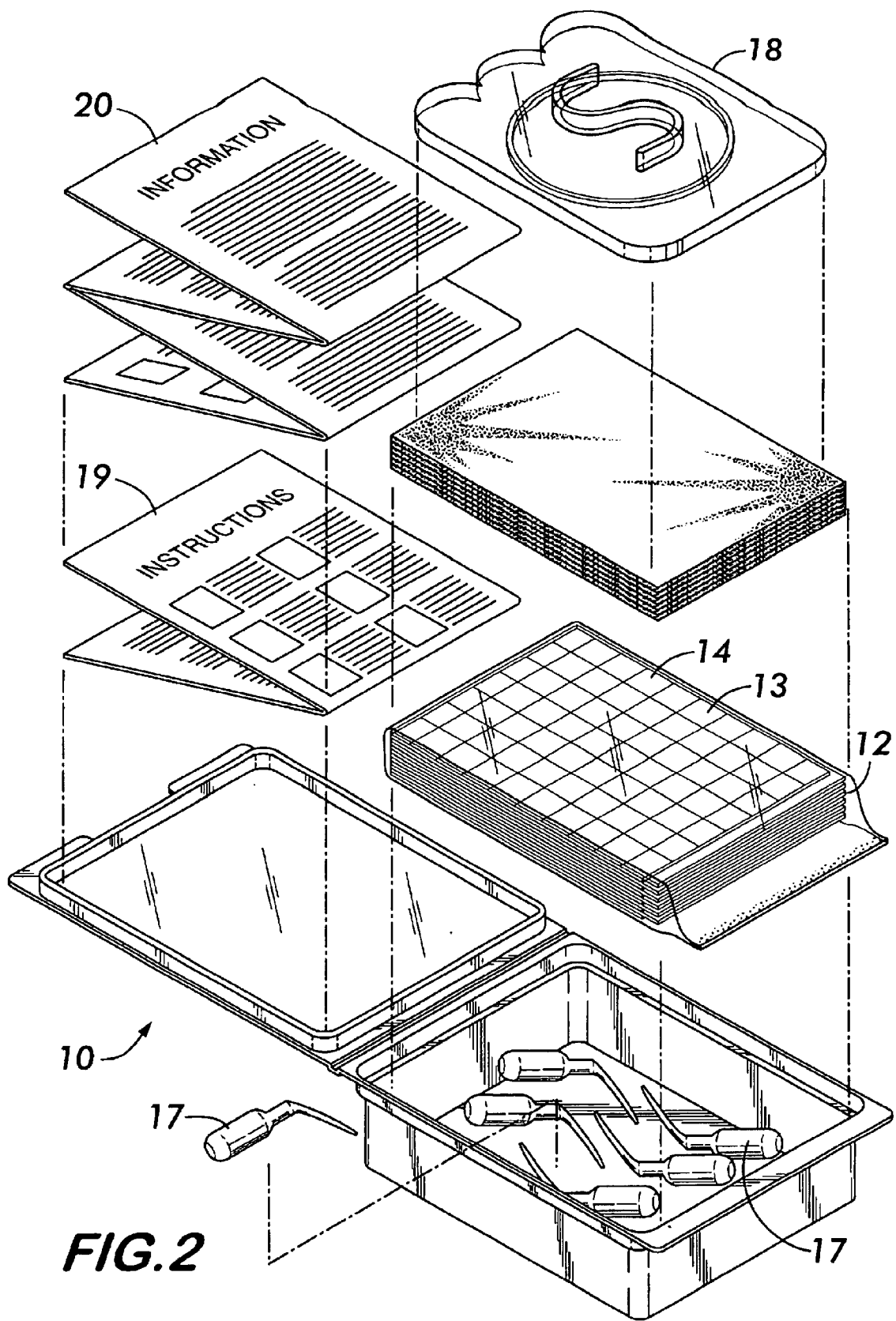
FIG. 2 is a view of the collection kit of FIG. 1 showing the contents of the collection kit.

With reference first to FIGS. 1 and 2, a kit 10 having the necessary components for practicing the method of the invention is disclosed. As explained in more detail hereinafter, the kit 10 comprises a packet containing a plurality of collection devices 12. Each collection device 12 may take various forms, a preferred form being marketed by 3M Company of St. Paul, Minn., under the trademark Petrifilm™. The Petrifilm™ collection device is one of a variety of dry collection devices having a surface shown at 13 in FIG. 3 on which a nutrient broth for producing microbiological growth has been pre-applied and allowed to dry. Preferably, the surface 13 is non-porous. The surface 13 is preferably preprinted with a grid shown at 14 in FIG. 3 which is visible through the nutrient medium so as to facilitate the counting of microorganism colonies. Each collection device 12 is preferably provided with a protective transparent film overlay shown at 15 in FIG. 3, the overlay being adhesively attached to collection device 12 along one edge thereof as illustrated at 16.

The kit 10 is further provided with a multiplicity of ampules 17 containing a premeasured volume of sterile buffered water or other activation fluid sufficient for hydrating the dehydrated culture medium on the surface 13 of collection device 12. Typically, the ampules 17 are supplied with sterile, buffered water. The kit 10 further comprises a suitable 20 hand press 18 utilized for dispersing the activating liquid from ampule 17 over a controlled area of the surface of collection device 12, as will be described in more detail hereinafter. Finally, the kit 10 comprises suitable instructions 19 and an information sheet 20.

With reference now to the embodiment shown in FIGS. 3–7, when the user is ready to test a room or other space for the presence of molds or other microorganisms, a collection device 12 is removed from the packet of collection devices and the transparent film layer is pulled back in order to expose the surface carrying the dry growth medium as well as the inner surface of the transparent film layer. In certain embodiments, the inner surface of transparent film layer is also considered a collection surface on which microorganisms are collected. In such embodiments, the inner surface of the transparent film layer has disposed thereon an adhesive, a dry growth medium or a mixture thereof. The collection device 12 is then placed on a surface in the location where microorganisms are suspected of being present. Strips of adhesive tape, as shown at 11 in FIG. 4, may be used to maintain the device in place with the film layer exposing the collection surfaces. The exposed collection device is preferably left in place for a period of about 0.5 hours to about 8 hours, and even more preferably from about 0.5 hours and about 2 hours, with during which airborne microorganisms will settle out and deposit themselves on the growth medium.

Figure 3:
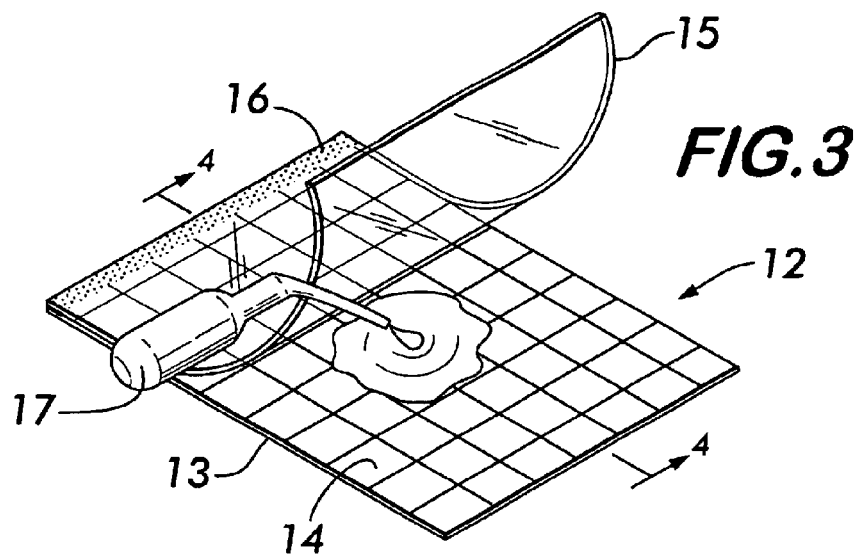
FIG. 3 is a top perspective view of a collection device bearing a dry growth medium with a premeasured volume of liquid being applied to the dry growth medium.
Figure 4:
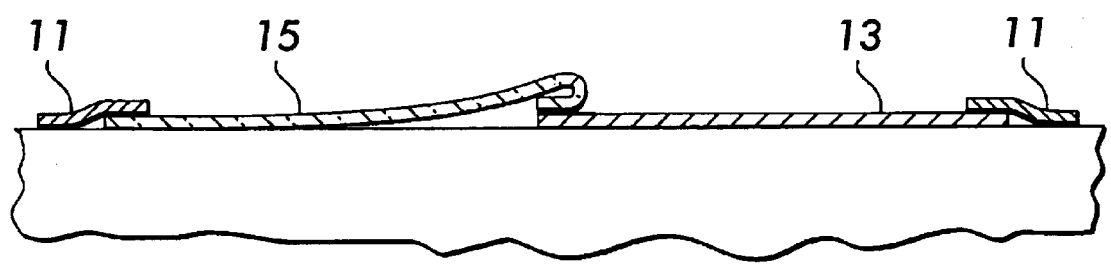
FIG. 4 is a cross sectional view of the device of FIG. 3 with the cover sheet open.
Figure 5:
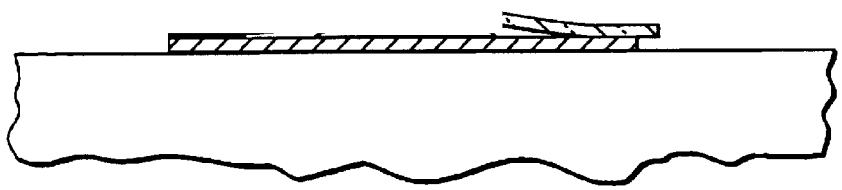
FIG. 5 is a cross sectional view of the device of FIG. 4 with the cover sheet closed around a premeasured volume of liquid.
Figure 6:
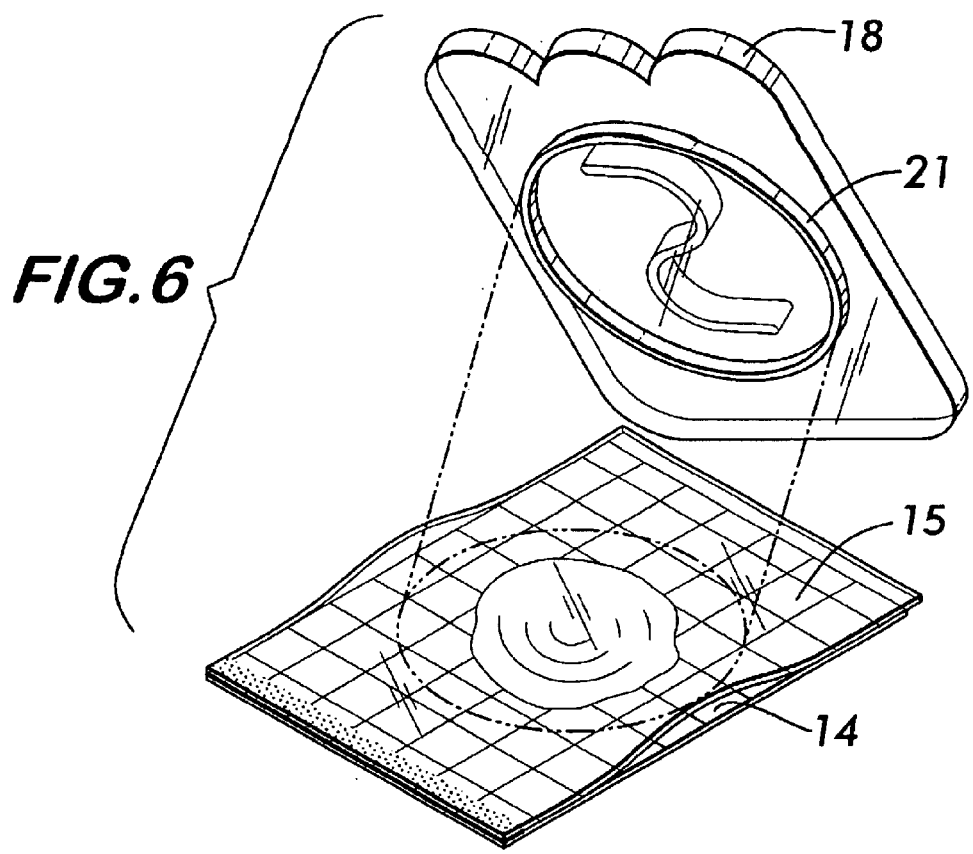
FIG. 6 is a top view of the device of FIG. 5 demonstrating the use of a hand press.

After a predetermined interval of time has elapsed, the collection period is concluded and the contents of an ampule 17 is then dispensed onto the surface 13 of collection device 12. As indicated in FIGS. 3 and 5, the transparent film layer is then placed over the activating liquid on the surface 13 of collection device 12, and as illustrated in FIG. 6, the hand press 18 is pressed down to disperse the liquid over the dry growth medium. As can be seen in FIG. 6, the applicator 18 is provided with an annular ring 21. When pressed downwardly, the activating liquid is dispersed to uniformly contact substantially all of the growth medium within the area defined by ring 21. In certain embodiments, the device is then placed in an aerobic container which is stored in a dry place, preferably at room temperature, so that the microorganisms will grow into visible colonies.

Figure 12:
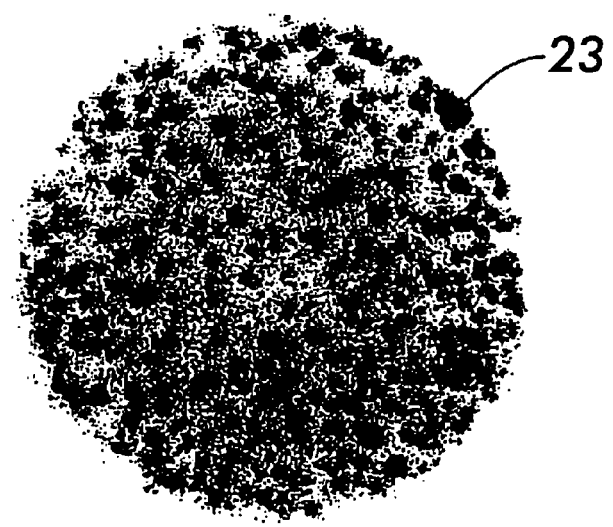
FIG. 12 is a top view of microorganism colonies grown on a collection device.

In a period of about 3–5 days, if any viable microorganisms were collected on the collection device, their colonies should become visible on its surface 13 as viewed through cover 15. FIG. 12 shows a typical population of microorganism colonies on a collection device following a period of about four days. In FIG. 12, the darkened areas 23 each indicate a mold colony. As can be seen in FIG. 12, adjacent colonies have begun to merge and, at this point, are ready to be counted. A sufficiently accurate count can thus be obtained by counting the number of dots, i.e., colonies, in a representative subset of the total number of squares of the grid printed on the collection device 12 within the circular area in which the culture medium has been activated. An average can be determined and multiplied by the total number of grids within the circular area to give an accurate estimate of the total count of microorganism colonies.

FIG. 8 shows an alternative form of available collection device which may be incorporated into the kit and used in the practice of the invention. According to FIG. 8, the substrate for the device comprises a single layer, non-porous plastic tape 24 of about 20–80 microns in thickness. The tape is provided with an adhesive layer 24a which is substantially non-inhibitory to the growth of the microorganisms intended to be collected. The adhesive may have additives incorporated in or on it which will aid in making the microbiological colonies more visually distinct and countable. Such additives can be antibiotics and dyes. The third layer 24b is a detachable cover layer which keeps the adhesive collection surface sterile. Finger tabs 24c may be used to hold the tape substrate while pulling off cover layer 24b. The tape of FIG. 8 is used in the method of the invention by removing the cover 24b and exposing the tape to air either actively in a volumetric sampler or passively by allowing the microorganisms to deposit themselves by gravity or by pressing the tape onto a surface After collection the device is activated by removing the cover 15 of Petrifilm™ or a similar device and placing the device with its adhesive collection face down onto the hydrated surface as shown in FIG. 3. The device now becomes the new cover over the growth medium and is pressed as described previously in FIG. 6.

FIG. 9 shows a further form of collection device useful in carrying out the invention. According to FIG. 9, a non-porous substrate, typically available in tape form, has a micro-porous layer 25 adhesively attached hereto. Layer 26 has a Gurley porosity of less than 50 seconds and most preferably 0.1–25 seconds where Gurley porosity is defined as the time required to pass 100 cc of air through 1.0 square inch of material at standard pressure. Layer 26 has an upper surface to which an adhesive layer comprised of an adhesive substantially non-inhibitory to the growth of microorganisms is applied. The adhesive may have additives incorporated in or on it which will aid in making the microbiological colonies more visually distinct and countable. Such additives can be antibiotics and dyes. A detachable cover layer 27 keeps the upper, adhesively coated surface of layer 26 substantially sterile. As in the device illustrated in FIG. 8, finger tabs 25a and 27a are held by the user when peeling the protective cover layer off at the initiation of collection. Microporous films and compound films of the type described are known to those of ordinary skill in the art and are as substantially as described in Example 23 of U.S. Pat. Nos. 4,539,256 and 5,089,413.

Figure 7:
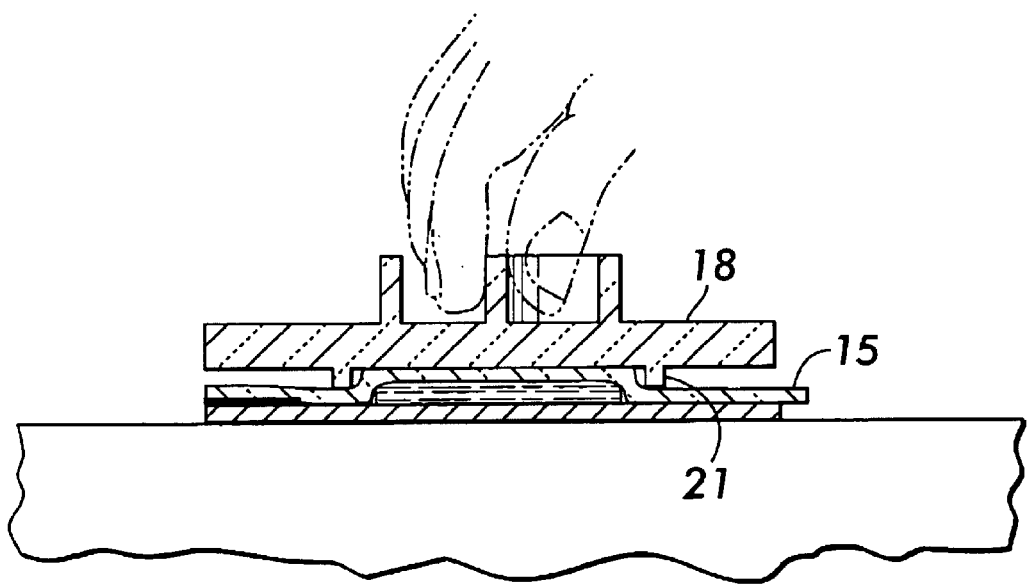
FIG. 7 is a cross sectional view of a hand press.

The collection device of FIG. 9 is used by removing cover layer 27 to expose the adhesively coated collection layer 26. At the completion of collection, the adhesively coated collection layer 26 is inverted and mounted on a hydrated device of the type shown in FIGS. 3–6, pressed as illustrated in FIG. 7 and incubated in the kit container. This dry collection device can also be activated after collection by mounting it with its collection race down directly on an agar surface or broth hydrated sterile pad. It is then incubated at an appropriate temperature and enumerated.

A further means and method of the invention are illustrated in FIG. 10. FIG. 10 shows a sterile dry collection device 30 encased within its protective enclosure 32. The device is a porous pad. The pad is attached to a double sided tape 31 which is permanently attached to the pad with an adhesive shown at 30a which is substantially non inhibitory to the growth of microorganisms. The other side of the double sided tape is releasably attached at 3 lb to the enclosure. After the pad 30 is removed from its enclosure and exposed to the air passively, or in an active volumetric sampler, or as a wipe sampler, it is returned to its enclosure or other sterile container, hydrated with between about 1–3 ml of an appropriate nutrient broth, the nutrient being appropriate to the microorganism to the cultured and in a quantity sufficient to hydrate substantially the matrix of the pad. The enclosure 32 is then resealed as shown at 32a to hold the hydrated pad within an aerobic, high humidity envelope. The device is incubated and enumerated according to standard methods.

Figure 11:
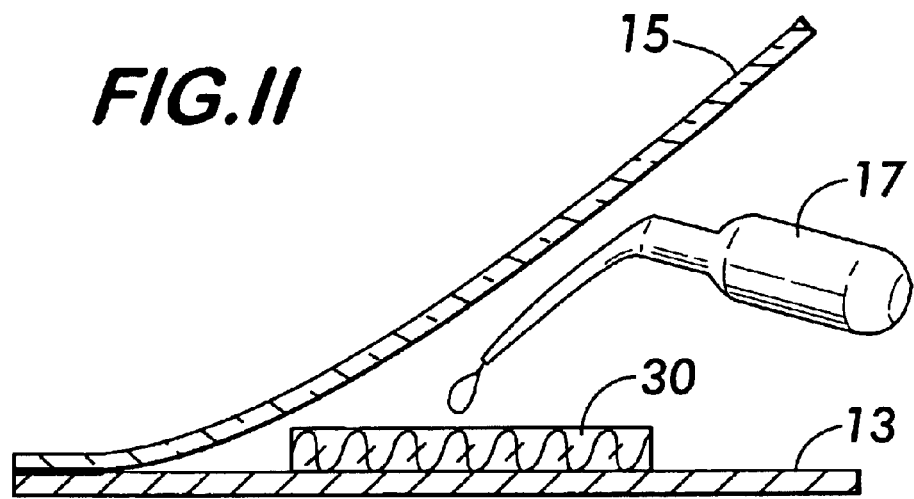
FIG. 11 is a cross sectional view of a dry collection device illustrating its use in conjunction with a collection pad.

FIG. 11 shows still a further method of hydrating a porous pad 30 which has been exposed to gravitational collection or used as a wipe sampler or submitted to active collection in a volumetric sampler. The porous pad 30 with the collection surface face down is placed on the culture-carrying surface 13 of the device of FIG. 3. The pad is then activated by hydrating using an ampule 17. The cover layer 15 is then closed and the hydrating agent is dispersed into the circle defined by the annular ring 21 on the hand press 18.

According to a preferred form of the kit useful for testing for microorganisms in a home, a packet of ten collection devices 12 is provided to allow for sampling in most rooms in a typically sized home. The use of the transparent cover layers 15 allows for stacking of the collection devices without risk of cross contamination during the incubation period.

The following examples are submitted to illustrate but not limit this invention.

EXAMPLES

Example 1

Petrifilm™ is used in this invention as a self-contained quantifiable dry collection device and growth and enumeration device. The Petrifilm™ is exposed to ambient air by lifting its top cover and peeling it back completely to its hinge with the bottom film. The top cover can be pulled partially away from the bottom film at their mutual adhesive hinge. This stretching of the hinge will allow the top cover to be laid back onto the surface and remain open during the sampling period. An adhesive tape may be used at the top and bottom edges of the open film in order to securely hold it open and in place.

At the end of the sampling period, the film is closed and removed to a flat, hard surface. The film is then reopened and hydrated with 1 ml of buffered water. The film is re-closed and a hand press is applied to the top of the film and the liquid is spread into a uniform circle between the top and bottom film. The film is incubated and enumerated as directed.

Example 2

A further dry collection method involves the use of single layer adhesive tapes. The tape can be used actively to sample a specific area of a surface, passively via gravitational collection of microorganisms from the air or as the capture film in a volumetric pump sampler. The tape is coated with an adhesive which is substantially non-inhibitory to the growth of microorganisms. The tape may also contain dyes and other ingredients such as antibiotics in order to limit the growth of certain organisms. An example of this type of film is the top cover sheet of Petrifilm™. Tapes of this type are well known to those skilled in the art.

These thin (20–40 microns) tapes, after a collection event, are transferred to and laid on various nutrient-coated surfaces for hydration, to initiate germination, growth and enumeration. The preferred nutrient-coated surfaces are porous pads and Petrifilm™ (3M Company, St. Paul, Minn.).

Example 3

Another dry collection method is the use of a multi-layered compound tape, the active collection surface of which is a micro-porous breathable adhesive film. The micro-porous breathable film is attached on one side to a non porous clear tape backing, creating the compound, clear tape. The outer surface of the micro-porous tape is coated with an adhesive which is substantially non-inhibitory to the growth of microorganisms. The micro-porous tape will preferably have a Gurley porosity between 0.1 and 25 seconds and may contain dyes, antibiotics or other chemical enhancements to aid in the germination, growth identification and visualization of the microorganisms.

The film is substantially the same in design to that of the bottom layer of Petrifilm™ as described in U.S. Pat. Nos. 4,565,783 and 5,089,413 and RE35,286. However, this film is unique in that it is not coated with a nutrient medium and its preferred thickness is 40–100 microns so that it can be easily deformed onto the irregularities of collection surfaces and can subsequently be compressed easily into a confined area of hydration when placed on its nutrient device. Compound films of this type are well known to those skilled in the art.

The film may be used actively or passively to collect microbes from air or surfaces. After collection, the film may be mounted on any agar surface or pad and hydrated with media broth or hydrated Petrifilm™.

Example 4

Collection pads made of various woven and non-woven natural and synthetic fibers which, after dry collection, are placed on hydrated nutrient agar surfaces or are hydrated with nutrient broths to initiate germination, growth and subsequent enumeration and quantification after the collection event. These collection pads are comprised of a complex web of micro-fibers which yield a rough textured capture surface relative to the size of the microorganisms as well as a deep complex capture web within the pads' structure. The micro-fibrous pads may also exhibit an electrostatic charge. These micro-fiber web pads are most suitable when air is turbulent or when the article or surface to which it is attached is in motion or an air stream is directed across it. The sterile pad is dispensed to the surface of interest from its packaging via forceps or sanitized gloved hand or attached tab. The pad may also be attached on one surface to one of the two tape devices described above or dispensed within its packaging envelope with one side exposed to the air.

At the completion of the pads' exposure period, it is aseptically lifted from its test side and (1) placed on media specific Petrifilm™, and hydrated, covered, pressed as shown in FIGS. 6, 7 and 11, and incubated for subsequent growth, enumeration, and quantification; or (2) inserted into a sterile, clear, deformable plastic bag container, and hydrated with organism-specific broth as shown in FIG. 10. The bag is pressed to spread the broth throughout the matrix. It is then incubated and enumerated as directed; or (3) it is hydrated with broth within the hydrophobic packaging unit in which it sits, the packaging unit is resealed, incubated and enumerated as directed; or (4) if the pad has a micro-porous backing film, it can be inverted and laid upon and pressed into fresh agar media, incubated and enumerated as directed; or (5) if the pad is attached to a micro porous compound adhesive film described above, it can be hydrated with appropriate nutrient broth and covered with an attaching layer of film which is affixed to the adhesive layer of the film surrounding the sample pad, thereby creating an aerated, sealed bubble-like chamber with a micro porous edge exposed to the air, which will keep the chamber aerobic.

All of the aforementioned dry collection devices have the advantage of enabling the practitioner to conduct long duration sampling times as compared to existing wet collection technologies which are limited to short duration exposures due to the agar desiccation and the resultant skinning over effect. These limitations are shown in the use of hydrated Petrifilm™ for the wet collection of environmental microbials which is recommended by the manufacturer to be limited to 15 minutes.

Most volumetric, active pump samplers acquire a limited volume of air in the range of 100 liters in one (1) or two (2) minutes. These short duration sampling periods proscribed by wet collection technologies greatly limits the usefulness of the data obtained to very narrow conclusions about overall air quality at the given test minute or 15 minutes. Furthermore, the equipment used in active pump sampling is extremely expensive as compared to the proposed devices of the present invention.

In addition, the active pump sampling technology can only take one sample at one location at a time, requiring a technician to be in attendance. The proposed invention allows a practitioner/user to conduct multiple tests at the same time in a variety of diverse test locations in order to do concurrent bioburden comparisons.

Example 5

The invention further provides for the construction of a kit which combines one or more of the collection and enumeration devices and all the pertinent parts thereto for consumer use, i.e., which is not limited in use to scientific practitioners skilled in the field of microbiology. The kit is composed of the following items:

a. A dry matrix which will actively or passively collect environmental air mold spores;

b. A sterile or non-sterile activating broth or re-hydrating liquid that will induce environmental air mold spores to germinate and grow on the matrix in the pattern density in which it was collected;

c. A container that may be used to store the activated matrices at an appropriate temperature range;

d. Detailed use directions, a self-help tutorial that describes how to visually enumerate environmental air mold colonies growing on the activated matrix;

e. Detailed instructions which may help the user to detect the source of the environmental air mold spores, and f. Detailed instructions which may help the user to clean up the source of the environmental air mold spores using general clean-up procedures and commercially available fungicides.

Having thus described a few particular embodiments of the invention, various alterations, modifications, and improvements will readily occur to those skilled in the art. Such alterations, modifications and improvements as are made obvious by this disclosure are intended to be part of this description though not expressly stated herein, and are intended to be within the spirit and scope of the invention. Accordingly, the foregoing description is by way of example only, and not limiting. The invention is limited only as defined in the following claims and equivalents thereto.

What is claimed is:

1. A method for detecting microorganisms, comprising the steps of:

(a) collecting microorganisms on a collection device bearing a dry growth medium by placement of the collection device on a surface for exposure to ambient air for a predetermined period of time;

(b) adding a premeasured volume of activating liquid to the dry growth medium after completion of the exposure step; and (c) allowing any collected microorganisms to grow into colonies.

2. The method of claim 1 wherein the method further comprises after step (b) and before step (c) the step of spreading the activating liquid over a predefined area of the medium with a hand press by placing the hand press over the liquid on the medium and applying sufficient pressure to spread the liquid over the predefined area of the medium.

3. The method of claim 1 wherein the device comprises a substrate having an upper surface and a layer of a dry growth medium disposed on the upper surface of the substrate.

4. The method of claim 1 wherein the device comprises a self-supporting, water-proof substrate having an upper surface, a layer of adhesive coated on the upper surface of the substrate, the adhesive being non-inhibitory to the growth of microorganisms, and cold-water-soluble powder adhered uniformly to the adhesive, the powder comprising one or more nutrients for growing microorganisms, and optionally a gelling agent.

5. The method of claim 3 wherein the device further comprises a cover sheet releasably adhered to at least a portion of the substrate the cover sheet being opened in step (a) to expose the dry growth medium to ambient air and closed in step (c) to allow collected microorganisms to grow.

6. The method of claim 3 wherein the adhesive layer is translucent to allow the colonies to be visually inspected.

7. The method of claim 1 wherein said device comprises:

a self-supporting, water-proof substrate having an upper surface; an air-permeable membrane having its peripheral edge(s) substantially uncovered, and having a top surface and a bottom surface, the bottom surface being fixed to and covering at least a portion of the upper surface of the substrate; and a dry growth medium fixed to and covering at least a portion of the top surface of the membrane comprising one or more nutrients for growing microorganisms, and optionally a gelling agent.

8. The method of claim 1 wherein the method further comprises an additional step between steps (b) and (c) of placing the device in an incubator.

9. The method of claim 3 wherein the powder comprises a gelling agent in an amount sufficient to form a gel having a Brookfield viscosity of at least 1500 cps when hydrated with the premeasured volume of water.

10. The method of claim 1 wherein the method further comprises an additional step after step (c) of counting the colonies.

* * * * *